(12) United States Patent
Sakamoto

(10) Patent No.: US 9,239,291 B2
(45) Date of Patent: Jan. 19, 2016

(54) DETECTOR

(71) Applicant: PANASONIC CORPORATION, Osaka (JP)

(72) Inventor: Koji Sakamoto, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 54 days.

(21) Appl. No.: 14/352,372

(22) PCT Filed: Oct. 16, 2012

(86) PCT No.: PCT/JP2012/076652
§ 371 (c)(1),
(2) Date: Apr. 17, 2014

(87) PCT Pub. No.: WO2013/061817
PCT Pub. Date: May 2, 2013

(65) Prior Publication Data
US 2014/0326889 A1   Nov. 6, 2014

(30) Foreign Application Priority Data
Oct. 24, 2011   (JP) ................................ 2011-232562

(51) Int. Cl.
*G01N 21/03* (2006.01)
*G01N 21/59* (2006.01)
*G01N 21/3504* (2014.01)

(52) U.S. Cl.
CPC .............. *G01N 21/59* (2013.01); *G01N 21/031* (2013.01); *G01N 21/0303* (2013.01); *G01N 21/3504* (2013.01)

(58) Field of Classification Search
CPC ............ G01N 21/0303; G01N 21/031; G01N 21/3504; G01N 21/59
See application file for complete search history.

(56) References Cited

U.S. PATENT DOCUMENTS 4,557,603 A   12/1985   Oehler et al.
4,662,755 A   5/1987   Aoki et al.
(Continued)

FOREIGN PATENT DOCUMENTS

CN   1426532   6/2003
CN   1735801   2/2006
(Continued)

OTHER PUBLICATIONS

Search report from E.P.O., mail date is Feb. 13, 2015.
(Continued)

*Primary Examiner* — Mark R Gaworecki
(74) *Attorney, Agent, or Firm* — Greenblum & Bernstein, P.L.C.

(57) ABSTRACT

The detector in accordance with the present invention includes: a light emitter; a light receiver; and a light guiding member which includes a detection space for determining a state of a predetermined gas and is configured to guide light emitted from the light emitter to the at least one light receiver through the detection space. An internal surface of the detection space of the light guiding member includes a reflective surface causing reflection of light emitted from the light emitter. The reflective surface is a concave ellipsoidal surface having a long axis defined by a straight line determined by the light emitter and the light receiver. The reflective surface has a first focal point at a position of the light emitter and a second focal point on an opposite side of the light receiver from the first focal point.

9 Claims, 7 Drawing Sheets

(56) References Cited

U.S. PATENT DOCUMENTS

| | | |
|---|---|---|
| 5,170,064 A | 12/1992 | Howe |
| 2003/0136911 A1 | 7/2003 | Martin |
| 2006/0219923 A1 | 10/2006 | Uchida et al. |
| 2006/0226367 A1 | 10/2006 | Hopkins et al. |
| 2007/0114421 A1 | 5/2007 | Maehlich et al. |
| 2009/0284745 A1 | 11/2009 | Yi |

FOREIGN PATENT DOCUMENTS

| | | |
|---|---|---|
| JP | 5-503352 | 6/1993 |
| JP | 05-215685 | 8/1993 |
| JP | 07-36051 | 7/1995 |
| JP | 07-036052 | 7/1995 |
| JP | 07-198609 | 8/1995 |
| JP | 9-229858 | 9/1997 |
| JP | 09-318528 | 12/1997 |
| JP | 63-304137 | 12/1998 |
| JP | 2002-350341 | 12/2002 |
| JP | 2006-275980 | 10/2006 |
| JP | 2007-147613 | 6/2007 |
| JP | 2007-212315 | 8/2007 |
| JP | 2008-517295 | 5/2008 |

OTHER PUBLICATIONS

Search report from PCT/JP2012/076652, mail date is Nov. 20, 2012.
Taiwan Search Report, Apr. 7, 2015.

DETECTOR

TECHNICAL FIELD

The present invention relates to detectors and particularly to a detector for determining a type or a concentration of gas, a concentration of smoke, or dust in gas.

BACKGROUND ART

In the past, there has been proposed a gas sensor including a gas measurement chamber, an infrared radiation source, and a detector for detecting infrared radiation. The gas measurement chamber includes an internal wall having a spheroidal shape.

The infrared radiation source is situated at a position of one of focal points inside the gas measurement chamber and the detector is situated at a position of the other focal point (see document 1 [JP 2007-147613 A]).

When a gas to be detected is present in the gas measurement chamber, infrared radiation having a specific wavelength corresponding to a type of the gas is absorbed. Therefore, it is possible to determine the composition of the gas present in the gas measurement chamber based on the magnitude of the infrared radiation detected by the detector.

Besides, document 2 (JP 2006-275980 A) discloses an infrared gas detector including a gas chamber, an infrared light emitting device, and an infrared detection device. The gas chamber has an ellipsoidal shape. The infrared light emitting device is situated at a position of one of focal points inside the gas chamber, and the infrared detection device is situated at a position of the other focal point.

As described above, according to the gas sensor of document 1 and the detector of document 2, light receiving elements are situated at the focal position. Hence, light rays reflected by the surface of such a spheroid can be focused into the light receiving element.

However, with regard to light (infrared light) that is reflected once by part of the surface of the spheroid close to the light receiving element and strikes the light receiving element, an incident angle of such light is larger.

Especially, in the aforementioned detector, an optical filter is situated in front of the light receiving element. The light striking the light receiving element at the larger incident angle also strikes the optical filter at a larger incident angle (i.e., an angle between an incident direction of light on the optical filter and an optical axis of the optical filter). With regard to the light striking the optical filter at the large incident angle, the optical filter is unlikely to show desired transmittance-wavelength characteristics. Consequently, an S/N ratio may be deteriorated. Additionally, an amount of light reflected by a surface of the optical filter is likely to increase.

SUMMARY OF INVENTION

In view of the above insufficiency, the object of the present invention is to propose a detector capable of decreasing an incident angle of light to a light receiver.

The detector of the first aspect in accordance with the present invention includes: a light emitter; at least one light receiver; and a light guiding member which includes a detection space for determining a state of a predetermined gas and is configured to guide light emitted from the light emitter to the at least one light receiver through the detection space. An internal surface of the detection space of the light guiding member includes at least one reflective surface causing reflection of light emitted from the light emitter. The at least one reflective surface is a concave ellipsoidal surface having a long axis defined by a straight line determined by the light emitter and the at least one light receiver. The at least one reflective surface has a first focal point at a position of the light emitter and a second focal point on an opposite side of the at least one light receiver from the first focal point.

According to the detector of the second aspect in accordance with the present invention, in addition to the first aspect, the detector comprises a plurality of light receivers. The at least one reflective surface is a concave ellipsoidal surface having a long axis defined by a straight line interconnecting a center of the plurality of light receivers and the light emitter.

According to the detector of the third aspect in accordance with the present invention, in addition to the first aspect, the detector includes a plurality of light receivers. The light guiding member including a plurality of reflective surfaces. The plurality of reflective surfaces are associated with the plurality of light receivers individually. Each of the plurality of reflective surfaces is a concave ellipsoidal surface having a long axis defined by a straight line interconnecting an associated one of the plurality of light receivers and the light emitter. Each of the plurality of reflective surfaces has the first focal point at the position of the light emitter and the second focal point on an opposite side of an associated one of the plurality of light receivers from the first focal point.

According to the detector of the fourth aspect in accordance with the present invention, in addition to the third aspect, the light guiding member includes a vent allowing the predetermined gas to transfer between the detection space and an external space. The vent is in a portion interconnecting the plurality of reflective surfaces.

According to the detector of the fifth aspect in accordance with the present invention, in addition to any one of the second to fourth aspects, the detector includes: a plurality of optical filters individually associated with the plurality of light receivers; and a detection unit. Each of the plurality of optical filters is between an associated one of the plurality of light receivers and the light emitter. Each of the plurality of light receivers is configured to supply an output corresponding to an amount of received light to the detection unit. The detection unit is configured to determine a state of the predetermined gas based on the outputs received from the plurality of light receivers.

According to the detector of the sixth aspect in accordance with the present invention, in addition to the fifth aspect, the plurality of optical filters have different transmission wavelength ranges.

According to the detector of the seventh aspect in accordance with the present invention, in addition to the fifth aspect, the plurality of optical filters have the same transmission wavelength range.

The detector of the eighth aspect in accordance with the present invention includes: a light emitter; a plurality of light receivers; and a light guiding member which includes a detection space for determining a state of a predetermined gas and is configured to guide light emitted from the light emitter to the plurality of light receivers through the detection space. An internal surface of the detection space of the light guiding member includes a plurality of reflective surfaces each causing reflection of light emitted from the light emitter. The plurality of reflective surfaces are associated with the plurality of light receivers individually. Each of the plurality of reflective surfaces is a concave ellipsoidal surface having a long axis defined by a straight line interconnecting an associated one of the plurality of light receivers and the light emitter. Each of the plurality of reflective surfaces has a first focal point at a position of the light emitter.

According to the detector of the ninth aspect in accordance with the present invention, in addition to the eighth aspect, each of the plurality of reflective surfaces has a second focal point on an opposite side of an associated one of the plurality of light receivers from the first focal point.

According to the detector of the tenth aspect in accordance with the present invention, in addition to the eighth aspect, each of the plurality of reflective surfaces has a second focal point at a position of an associated one of the plurality of light receivers.

According to the detector of the eleventh aspect in accordance with the present invention, in addition to any one of the eighth to tenth aspects, the light guiding member includes a vent allowing the predetermined gas to transfer between the detection space and an external space. The vent is in a portion interconnecting the plurality of reflective surfaces.

According to the detector of the twelfth aspect in accordance with the present invention, in addition to any one of the eighth to eleventh aspects, the detector includes: a plurality of optical filters individually associated with the plurality of light receivers; and a detection unit. Each of the plurality of optical filters is between an associated one of the plurality of light receivers and the light emitter. Each of the plurality of light receivers is configured to supply an output corresponding to an amount of received light to the detection unit. The detection unit is configured to determine a state of the predetermined gas based on the outputs received from the plurality of light receivers.

According to the detector of the thirteenth aspect in accordance with the present invention, in addition to the twelfth aspect, the plurality of optical filters have different transmission wavelength ranges.

According to the detector of the fourteenth aspect in accordance with the present invention, in addition to the twelfth aspect, the plurality of optical filters have the same transmission wavelength range.

DESCRIPTION OF EMBODIMENTS

Figure 1:
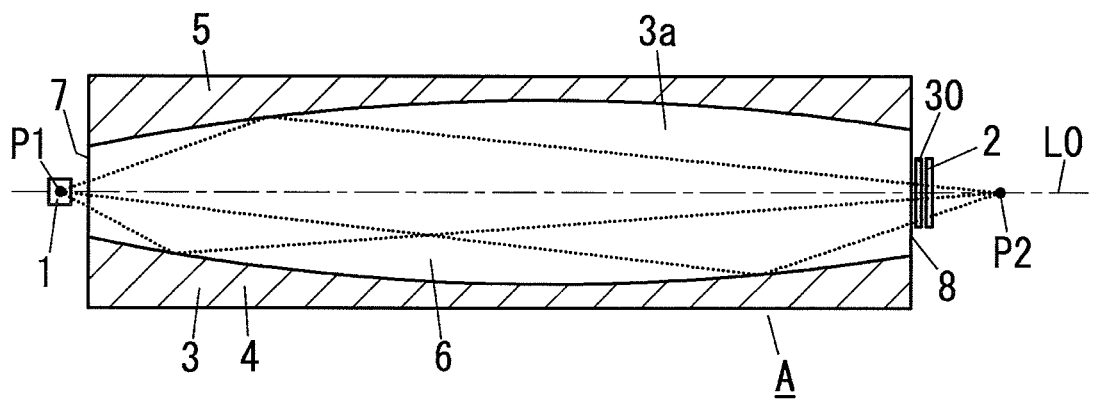
FIG. 1 is a schematic sectional view illustrating the detector of the present embodiment.

Hereinafter, the embodiment of the detector in accordance with the present invention is described with reference to FIGS. 1 to 12.

The detector A of the present embodiment is used to determine a type and a concentration of gas to be detected (e.g., carbon monoxide and methane). The detector A is not limited to a detector for determining a type and a concentration of gas, but may be a detector for determining presence or absence of smoke or dust and a concentration thereof.

As shown in FIGS. 1, 2, 4 to 6, the detector A includes: a light emitter 1, a light receiver 2, a light guiding member 3, a holder 10, a holder 20, and an optical filter 30. The light guiding member 3 has a circular cylindrical shape, and is constituted by a lower mirror 4 and an upper mirror 5. The holder 10 holds the light emitter 1. The holder 20 holds the light receiver 2.

The light guiding member 3 includes a detection space (internal space) 3a for determining a state of a predetermined gas. The light guiding member 3 is configured to guide light emitted from the light emitter 1 to the light receiver 2 through the detection space 3a. The detection space 3a of the light guiding member 3 has an internal surface that includes a reflective surface 6 to cause reflection of light emitted from the light emitter 1.

Figure 2:
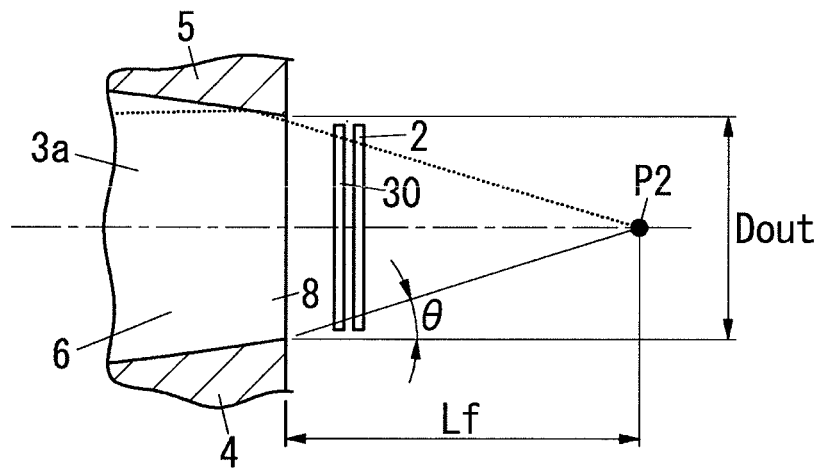
FIG. 2 is a partial sectional view illustrating the detector of the present embodiment.

The reflective surface 6 is a concave ellipsoidal surface having a long axis defined by a straight line (in the instance shown in FIG. 1, a straight line interconnecting a center of the light emitter 1 and a center of the light receiver 2) L0 determined by the light emitter 1 and the light receiver 2. The reflective surface 6 has a focal point (first focal point) at a position of the light emitter 1 and a focal point (second focal point) on an opposite side of the light receiver 2 from the focal point (first focal point). In FIGS. 1 and 2, the position of the first focal point is indicated by a focal position P1, and the position of the second focal point is indicated by a focal position P2.

The light guiding member 3 is formed into a hollow prismatic shape (in the present embodiment, a circular hollow prismatic shape). The light guiding member 3 has an opening (first opening) close to the first focal point, and an opening (second opening) close to the second focal point. The light guiding member 3 is configured to guide light entering an inside of the light guiding member 3 via the first opening to an outside of the light guiding member 3 via the second opening.

It is not necessary that the position (focal position) P1 of the first focal point of the reflective surface 6 is the same as the position of the light emitter 1 in a strict sense. It is allowed that the position P1 is substantially the same as the position of the light emitter 1.

For example, as shown in FIG. 2, the position P2 of the second focal point is determined such that an angle θ is not greater than 25°. The angle θ is an angle of a straight line interconnecting an edge of the second opening (exit side opening) of the light guiding member 3 and the second focal point relative to a central axis (long axis of the reflective surface 6) of the light guiding member 3. The angle θ is equal to $\tan^{-1}\{Dout/(2Lf)\}$. Lf is a distance between the second opening of the light guiding member 3 and the second focal point. Dout is a diameter of the second opening of the light guiding member 3.

It is preferable that the light receiver 2 be close to the second opening of the light guiding member 3 as possible. As the light receiver 2 is closer to the second opening of the light guiding member 3, an amount of light emitted outside via a gap between the light receiver 2 and the second opening of the light guiding member 3 can be more decreased.

An increase in a distance between the light emitter 1 and the light receiver 2 enables an increase in a length of a path along which light from the light emitter 1 passes through the detection space 3a of the light guiding member 3 (i.e., an increase in a major axis of the reflective surface 6) can be increased with an increase in a distance between the light emitter 1 and the light receiver 2. Hence, it is possible to more attenuate light from the light emitter 1. Thus, the sensitivity can be improved.

When a minor axis of the reflective surface 6 is constant, an increase in the major axis of the reflective surface 6 causes a decrease in a diameter of the first opening of the light guiding member 3. Hence, to obtain an enough amount of light (incident light amount) entering the detection space 3a through the first opening of the light guiding member 3 from the light emitter 1, it is necessary to increase the minor axis of the reflective surface 6. This causes an increase in size of the light guiding member 3.

To obtain both prevention of an increase in the size of the light guiding member 3 and improvement of the sensitivity, it is preferable that the distance between the light emitter 1 and the light receiver 2 be in a range of 10 to 150 mm. Preferably, the position P2 of the second focal point is adjusted so as to allow portions of a surface (light receiving surface) of the light receiver 2 to receive the same amount of light (light passing through the light guiding member 3). In this case, a change in a total amount of light striking the light receiver 2 caused by displacement of the light receiver 2 is reduced. It is possible to reduce a variation of a performance depending on an individual product. Hence, the yield rate can be increased, and the productive efficiency can be improved.

In the present embodiment, for example, the light guiding member 3 is a molded product of synthetic resin and has a circular cylindrical shape as a whole. The light guiding member 3 is constituted by the lower mirror 4 and the upper mirror 5 that have the same shapes as two parts obtained by dividing the shape of the light guiding member 3 by a plane that contains the central axis of the light guiding member 3 and is parallel to the central axis of the light guiding member 3.

The lower mirror 4 and the upper mirror 5 include bonding surfaces provided with recesses that constitute an ellipsoidal space when the lower mirror 4 and the upper mirror 5 are bonded to each other. The reflective surface 6 is formed by coating inner surfaces of the recesses with high reflective metal (e.g., by plating the inner surfaces of the recesses with chromium).

The lower mirror 4 and the upper mirror 5 have recesses 4a and 5a having hemispherical shapes, respectively. The recesses 4a and 5a are respectively formed in the bonding surfaces of the lower mirror 4 and the upper mirror 5 so as to be at a first end of the light guiding member 3 in an axial direction thereof and face each other. The recesses 4a and 5a constitute a through hole 7 when the lower mirror 4 and the upper mirror 5 are bonded to each other.

The lower mirror 4 and the upper mirror 5 have recesses 4b and 5b having hemispherical shapes, respectively. The recesses 4b and 5b are respectively formed in the bonding surfaces of the lower mirror 4 and the upper mirror 5 so as to be at a second end of the light guiding member 3 in the axial direction and face each other. The recesses 4b and 5b constitute a through hole 8 when the lower mirror 4 and the upper mirror 5 are bonded to each other.

The lower mirror 4 and the upper mirror 5 have recesses 4c and 5c having hemispherical shapes, respectively. The recesses 4c and 5c are respectively formed in portions of the lower mirror 4 and the upper mirror 5 corresponding to a peripheral surface of the light guiding member 3 to face each other. Each set of the recesses 4c and 5c constitute a vent 9 when the lower mirror 4 and the upper mirror 5 are bonded to each other.

The light emitter 1 includes a light emitting element 1a, a base 1b, and a plurality of terminal pins 1c. The light emitting element 1a is a light emitting diode for emitting infrared light, for example. The light emitting element 1a is mounted on a front surface of the base 1b having a disc shape. The plurality of terminal pins 1c are provided to a rear surface of the base 1b.

The light emitter 1 is attached to the first end of the light guiding member 3 in the axial direction by the holder 10 constituted by a cap 11 and a pressing plate 12.

The cap 11 has an approximate disc shape. The cap 11 is provided with a recess 11a in a surface close to the light guiding member 3. The recess 11a has a circular hole shape to receive the end of the light guiding member 3. In a center of a bottom of the recess 11a, a circular hole 11b is formed to communicate to the through hole 7 of the light guiding member 3. Further, the cap 11 is provided with a recess 11c in a further surface away from the light guiding member 3. The recess 11c is in a vicinity of the circular hole 11b, and receives the base 1b of the light emitter 1.

The pressing plate 12 has an approximate disc shape. The pressing plate 12 is provided with through holes 12a in a center thereof. The through holes 12a allow the terminal pins 1c of the light emitter 1 to pass therethrough. Note that, each through hole 12a has an inner diameter less than an outer diameter of the base 1b, and the pressing plate 12 has an outer diameter greater than the outer diameter of the base 1b.

The light receiver 2 includes a can-type body 2b. There are light receiving windows 2c formed in a front surface of the body 2b, and light receiving elements 2a are inside the body 2b to face the individual light receiving windows 2c. The light receiving elements 2a are pyroelectric infrared detection elements, for example. Further, there are a plurality of terminal pins 2d provided to a rear surface of the body 2b.

The light receiver 2 is attached to the second end of the light guiding member 3 in the axial direction by the holder 20 constituted by a cap 21 and a pressing plate 22.

The cap 21 has an approximate disc shape. The cap 21 is provided with a recess 21a in a surface close to the light guiding member 3. The recess 21a has a circular hole shape to receive the end of the light guiding member 3. In a center of a bottom of the recess 21a, a circular hole 21b is formed to communicate to the through hole 8 of the light guiding member 3.

The pressing plate 22 has an approximate disc shape. The pressing plate 22 is provided with through holes 22a in a center thereof. The through holes 22a allow the terminal pins 2d of the light receiver 2 to pass therethrough. Note that, each through hole 22a has an inner diameter less than an outer diameter of the body 2b of the light receiver 2, and the pressing plate 22 has an outer diameter greater than the outer diameter of the body 2b.

The optical filter 30 has a film shape. The optical filter 30 has such transmittance-wavelength characteristics that a transmittance becomes lower at a wavelength that is not in a wavelength range of light to be absorbed by a gas to be detected. The optical filter 30 is in front of the light receiver 2.

Alternatively, the optical filter 30 may be fixed to the body 2b of the light receiver 2 to be in front of the light receiving element 2a.

Hereinafter, assembly of this detector A is described.

First, an assembler assembles the light guiding member 3 from the lower mirror 4 and the upper mirror 5. Subsequently, the assembler attaches the cap 11 to the first end (the end provided with the through hole 7) of the light guiding member 3 in the axial direction, and attaches the cap 21 to the second end (the end provided with the through hole 8) of the light guiding member 3 in the axial direction.

Thereafter, the assembler situates the light emitter 1 inside the recess 11c such that a light emitting surface of the light emitter 1 faces the light guiding member 3. Then the assembler situates the pressing plate 12 behind the light emitter 1.

Attaching screws (not shown) are screwed into individual screw holes 4d and 5d of the light guiding member 3 by way of holes 12b and 11d of the pressing plate 12 and the cap 11, and thus the holder 10 is fixed to the light guiding member 3. Consequently, the light emitter 1 is held between the holder 10 and the light guiding member 3.

Additionally, the assembler situates the light receiver 2 inside the circular hole 21b such that the light receiving surface of the light receiver 2 faces the light guiding member 3. Then the assembler situates the pressing plate 22 behind the light receiver 2.

Furthermore, attaching screws (not shown) are screwed into individual screw holes of the light guiding member 3 by way of holes 22b and 21c of the pressing plate 22 and the cap 21, and thus the holder 20 is fixed to the light guiding member 3. Consequently, the light receiver 2 is held between the holder 20 and the light guiding member 3.

After the light emitter 1 and the light receiver 2 are attached to the light guiding member 3 by use of the holder 10 and the holder 20 respectively, the light emitting element 1a faces the through hole 7 and the light receiving element 2a faces the through hole 8. Light emitted from the light emitting element 1a comes into the internal space of the light guiding member 3, and directly strikes the light receiving element 2a or is reflected by the reflective surface 6 to strike the light receiving element 2a.

In order to detect a gas to be detected by use of this detector A, first the detector A is energized. Thus, the light emitting element 1a of the light emitter 1 emits light to the internal space of the light guiding member 3. The light emitter 1 is situated at the focal position P1 of the reflective surface 6 having an ellipsoidal shape and therefore reflected light rays caused by reflection of light rays emitted from the light emitter 1 at the reflective surface 6 are focused into the further focal position P2.

With regard to a straight line interconnecting the focal points P1 and P2, the light receiver 2 is closer to the light emitter 1 than the focal position P2 is. Hence, reflected light caused by reflection at the reflective surface 6 passes through the optical filter 30 and then enters the light receiver 2, and thus the light receiver 2 outputs a signal (a current signal or a voltage signal) having a magnitude proportional to an amount of received light.

When the gas to be detected comes into the internal space of the light guiding member 3 through the vents 9, a concentration of the gas to be detected increases. This causes an increase in an amount of light to be absorbed by this gas, and thus an amount of incident light on the light receiver 2 decreases. Such a decrease in the amount of the incident light on the light receiver 2 causes a change in the magnitude of the signal outputted from the light receiver 2. Hence, by use of the output signal from the light receiver 2, it is possible to determine the presence or absence of the gas to be detected, or the concentration of this gas.

Figure 9:
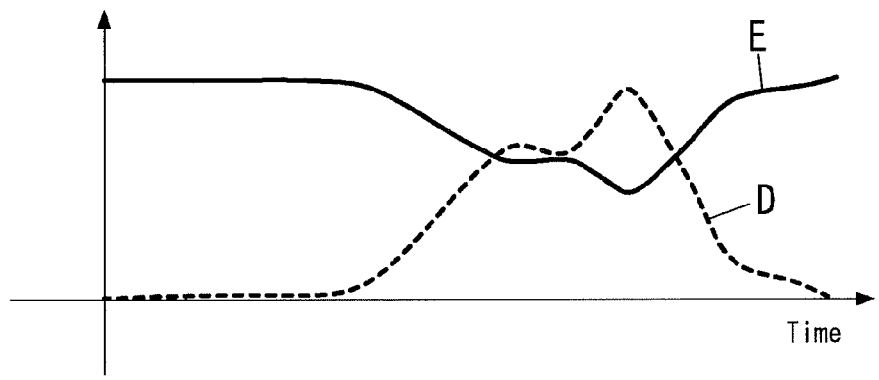
FIG. 9 is an explanatory diagram illustrating the waveform of the output from the light receiver of the detector of the present embodiment.

FIG. 9 shows measurement results of time variations of the concentration of the gas to be detected and the amount of the incident light on the light receiver 2. In this drawing, the line D indicates the concentration of the gas, and the line E indicates the amount of the incident light on the light receiver 2. The amount of the incident light decreases with an increase in the concentration and increases with a decrease in the concentration.

In this regard, as shown in FIG. 1, the reflective surface 6 of the present embodiment is formed into an ellipsoidal shape, the light emitter 1 is situated at one focal position P1 of the reflective surface 6, and the light receiver 2 is situated on a close side of the other focal position P2 to the light emitter 1.

The light emitter 1 is situated at one focal point P1 of the reflective surface 6 and therefore light rays emitted from the light emitter 1 are reflected by the reflective surface 6 and focused into the other focal point P2.

Figure 3:
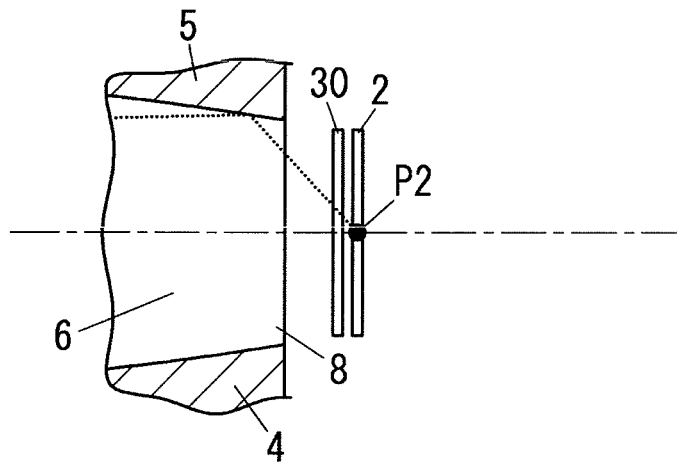
FIG. 3 is a partial sectional view illustrating the detector of the comparative example.
Figure 4:
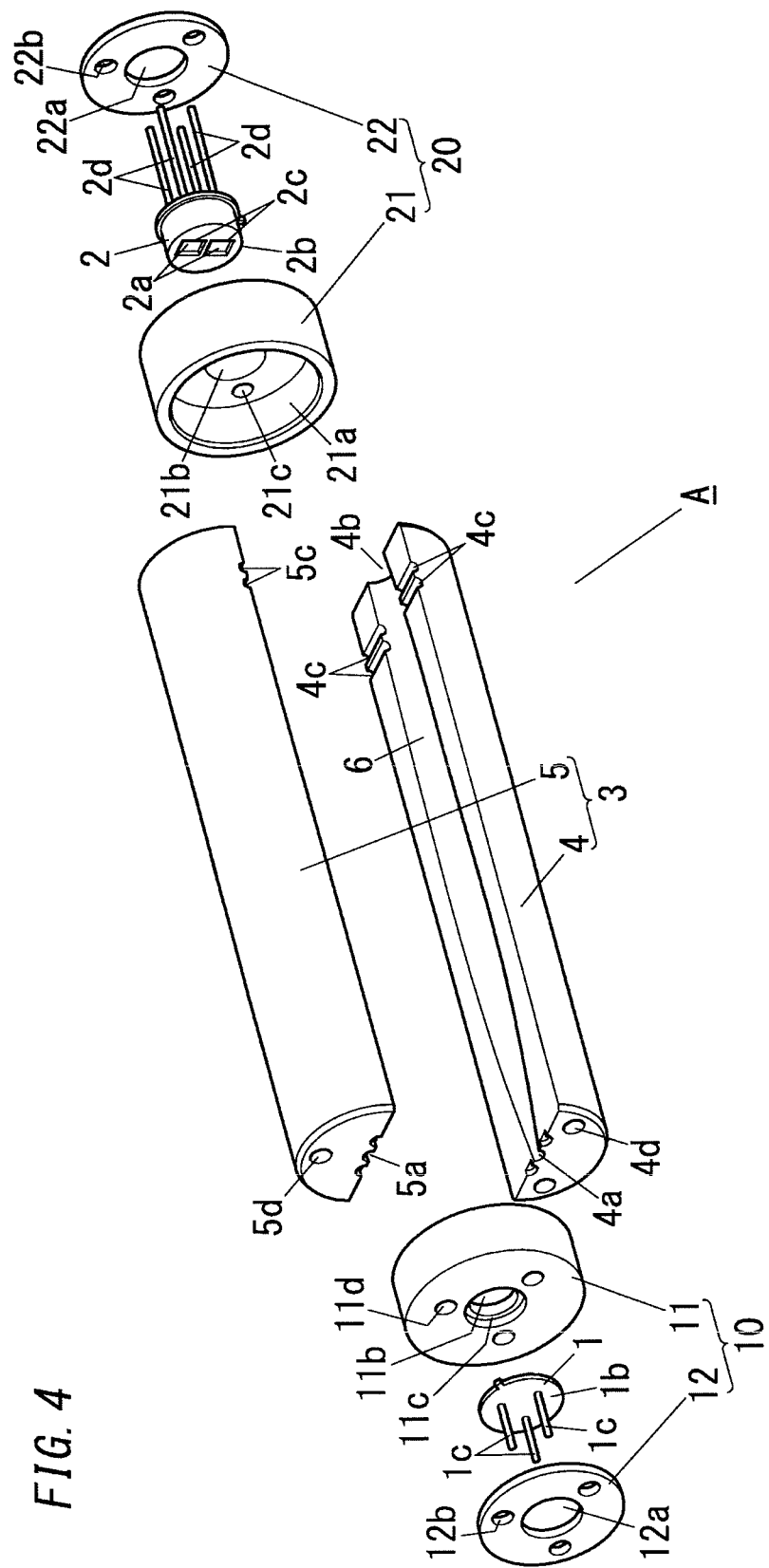
FIG. 4 is an exploded perspective view illustrating the detector of the present embodiment.
Figure 5:
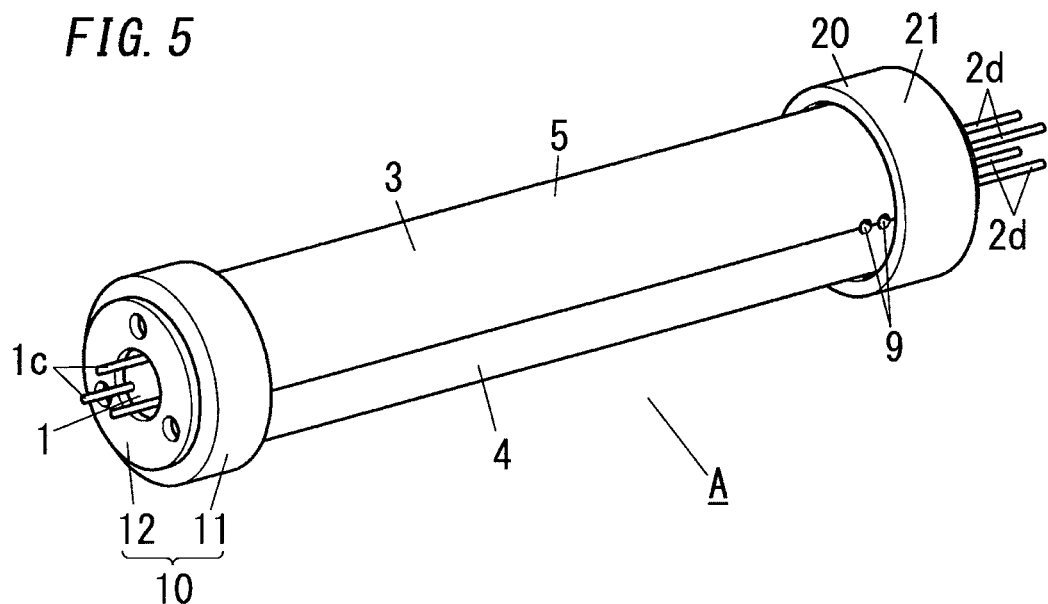
FIG. 5 is a perspective view illustrating the detector of the present embodiment.
Figure 6:
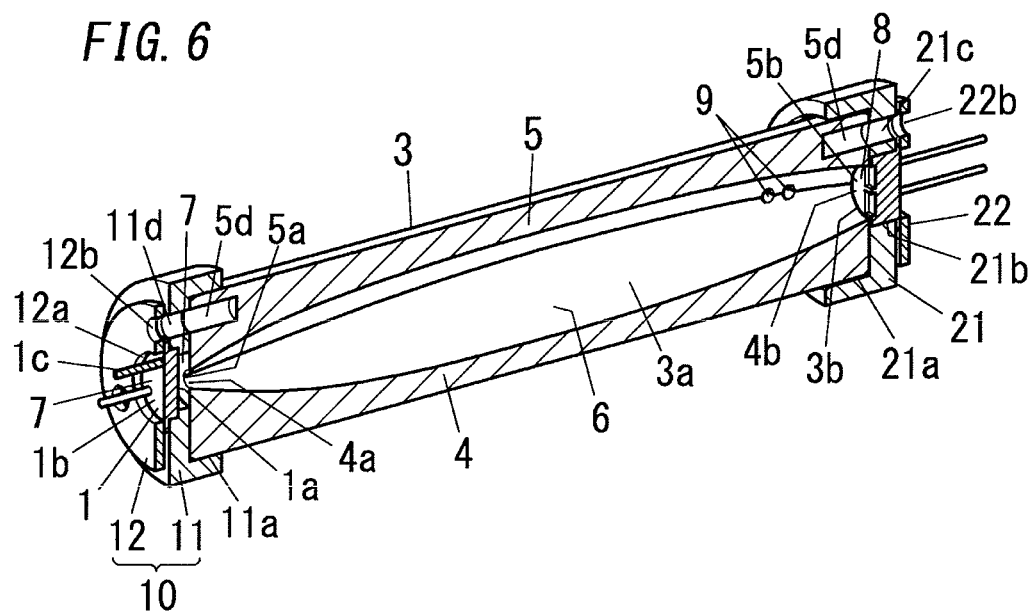
FIG. 6 is a perspective sectional view illustrating the detector of the present embodiment.

The light receiver 2 is situated on the close side of the further focal point P2 to the light emitter 1. Hence, an incident angle of light entering the light receiver 2 in this embodiment can be less than in the case where the light receiver 2 is situated at the focal position P2 as shown in FIG. 3 (see FIG. 2).

In contrast to a case where the incident angle is larger, it is possible to reduce a loss caused by reflection of incident light at the surface of the light receiver 2, and therefore the amount of the incident light on the light receiver 2 can be increased.

Besides, a wavelength range (hereinafter referred to as "absorption wavelength range") of light to be absorbed by gas depends on a type of gas, and the absorption wavelength range is inherent to the gas to be detected. In the present embodiment, situated in front of the light receiver 2 is the optical filter 30. The optical filter 30 has a transmittance that is higher in a wavelength range (absorption wavelength range) of light to be absorbed by the gas to be detected than in a wavelength range other than the absorption wavelength range. Thus, light that is not in the absorption wavelength range is attenuated by the optical filter 30, and therefore it is possible to successfully determine by use of the light receiving element 2a whether light in the absorption wavelength range exists. Consequently, the S/N ratio can be improved.

Figure 7:
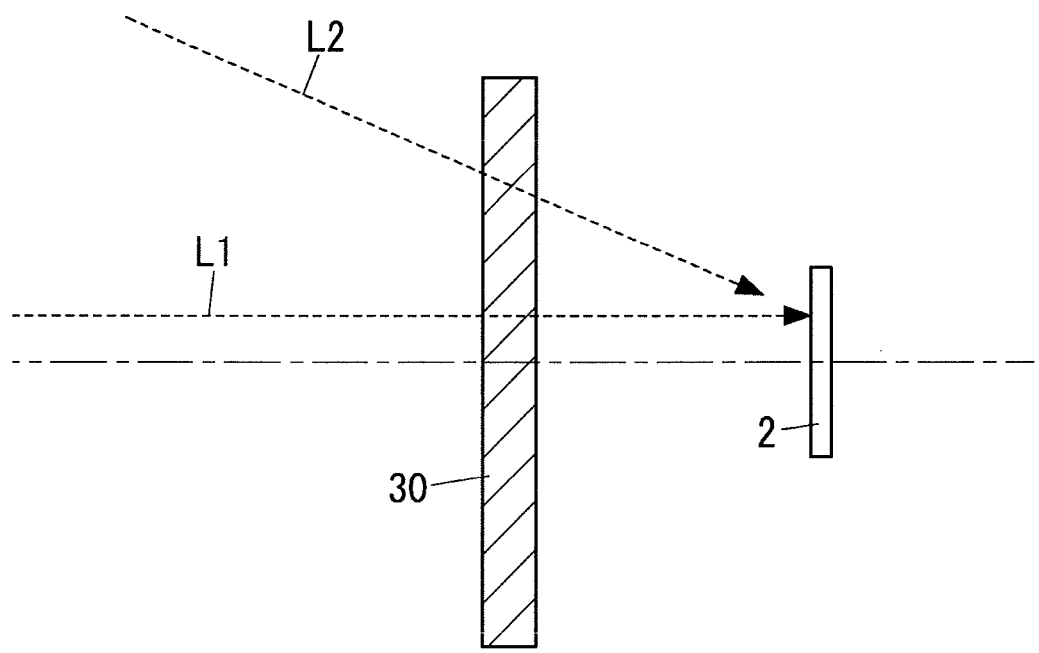
FIG. 7 is an explanatory diagram illustrating the path of the incident light on the optical filter of the detector of the present embodiment.

FIG. 7 shows a path of light that passes through the optical filter 30 and then strikes the light receiver 2.

A light ray L1 approximately orthogonally incident on the optical filter 30 is different from a light ray L2 obliquely incident on the optical filter 30 in a length of a path of light passing through the filter. The optical filter 30 shows different transmittance characteristics for the light rays L1 and L2.

Figure 8:
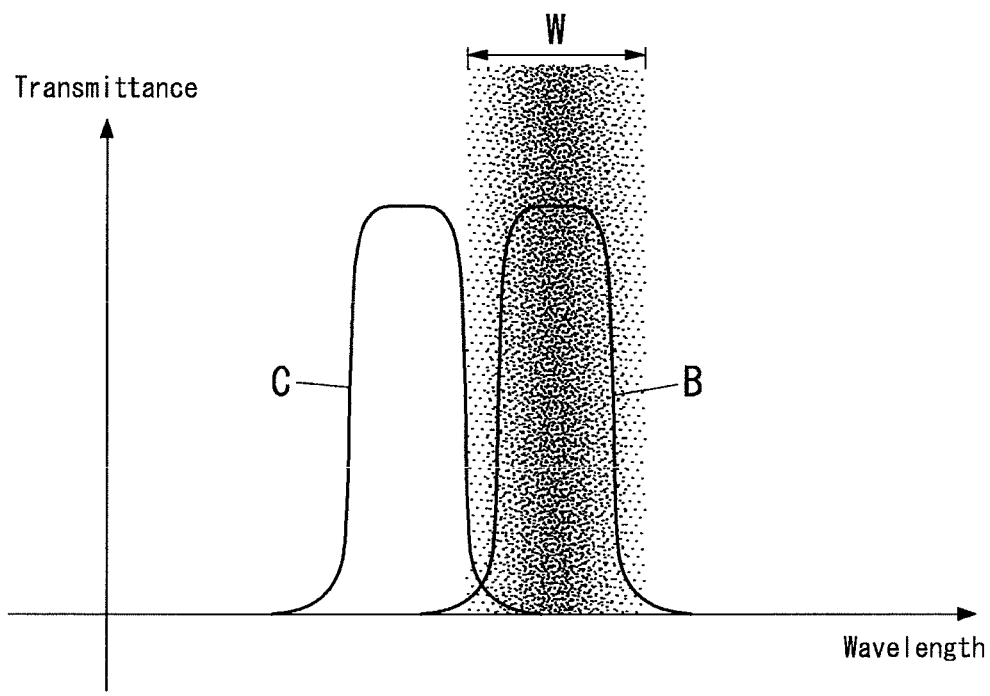
FIG. 8 is an explanatory diagram illustrating the transmittance-wavelength characteristics of the optical filter of the detector of the present embodiment.

FIG. 8 shows the transmittance-wavelength characteristics of the optical filter 30. The optical filter 30 is configured to have such transmittance-wavelength characteristics B that the transmittance becomes low at a wavelength which is not in an absorption wavelength range of the gas to be detected.

The optical filter 30 shows the transmittance-wavelength characteristics indicated by the line B with regard to the light ray L1 approximately orthogonally incident on the optical filter 30. Consequently, the optical filter 30 can attenuate light that is not in the absorption wavelength range.

Whereas, the length of the path of the light passing though the filter is greater in the light ray L2 than in the light ray L1, and the peak of the transmittance is deviated toward the short wavelength side. Consequently, the optical filter 30 shows the transmittance-wavelength characteristics indicated by the line C with regard to the light ray L2 obliquely incident on the optical filter 30.

In this case, the transmittance in the absorption wavelength range of the gas to be detected decreases, and the transmittance is higher in the short wavelength range than in the absorption wavelength range. Consequently, light of a wavelength desired to be transmitted is attenuated, but light of a wavelength desired not to be transmitted is transmitted. Hence, the S/N ratio is likely to decrease.

However, in the present embodiment, the light receiver 2 is situated on the close side of the focal point P1 to the light emitter 1 with regard to the straight line interconnecting the focal points P1 and P2. Thus, the incident angle of light striking the optical filter 30 can be decreased. Therefore, it is possible to reduce a change in the transmittance-wavelength characteristics with regard to the absorption wavelength range of the gas to be detected. Thus, the desired transmittance-wavelength characteristics are obtained. Consequently, a decrease in the S/N ratio can be reduced, and it is possible to successfully detect the gas to be detected.

In the schematic sectional view of FIG. 1, the number of light receives 2 is only one. However, like the first modification of the detector A of the present embodiment shown in FIG. 10, a plurality of (e.g., two) light receivers 2 (2A and 2B) may be provided. Additionally, a plurality of optical filters 30 (31 and 32) that have different transmission wavelength ranges may be situated in front of the light receivers 2A and 2B, respectively.

In more detail, the first modification of the detector A of the present embodiment includes a plurality of light receivers 2. The reflective surface 6 is a concave ellipsoidal surface having a long axis defined by a straight line interconnecting a center of the plurality of light receivers 2 (2A and 2B) and the light emitter 1. In the first modification, the center of the plurality of light receivers 2 (2A and 2B) is a midpoint between the light receivers 2A and 2B in a direction (upward and downward direction in FIG. 10) perpendicular to the axial direction (left and right direction in FIG. 10) of the light guiding member 3.

Additionally, the first modification of the detector A of the present embodiment includes the plurality of optical filters 30 (31 and 32) individually associated with the plurality of light receivers 2 (2A and 2B), and a detection unit 40. Each of the plurality of optical filters 30 is between an associated one of the plurality of light receivers 2 and the light emitter 1. Each of the plurality of light receivers 2 is configured to supply an output corresponding to an amount of received light to the detection unit 40. The detection unit 40 is configured to determine a state of the predetermined gas based on the outputs received from the plurality of light receivers 2.

In the first modification of the detector A of the present embodiment, the outputs from the light receivers 2A and 2B are inputted into the calculator 40 (the detection unit) constituted by a microcomputer, for example.

The calculator 40 determines the state of the gas to be detected, with reference to the amounts of the light received by the plurality of light receivers 2A and 2B. Note that, the state of the gas to be detected determined by the calculator (detection unit) 40 is, for example, the presence or absence of the gas to be detected in the internal space and the concentration of the gas to be detected. When there are a plurality of gasses to be detected, the state may be types of gasses present in the internal space.

The light emitter 1 is situated on the focal point P1 of the reflective surface 6. The light receivers 2A and 2B are situated on the close side of the further focal point P2 of the reflective surface 6 to the light emitter 1, and are between the through hole 8 of the light guiding member 3 and the focal point P2.

The optical filter 31 is in front of the light receiver 2A, and the optical filter 32 is in front of the light receiver 2B. The optical filter 31 is an optical bandpass filter for detection, and this bandpass filter transmits light within substantially the same wavelength range as the absorption wavelength range of the gas to be detected. The optical filter 32 is an optical bandpass filter for reference, and this bandpass filter transmits light within a different wavelength range from the wavelength range of the optical filter 31. In short, in the first modification of the detector A of the present embodiment, the plurality of optical filters 30 (31 and 32) have different transmission wavelength ranges.

The calculator 40 calculates a difference between the amount of the received light of the light receiver 2A calculated from the output from the light receiver 2A and the amount of the received light of the light receiver 2B calculated from the output from the light receiver 2B, and determines the presence or absence of the gas to be detected and the concentration thereof based on the calculated difference.

When the gas to be detected flows into the internal space of the light guiding member 3, the amount of the light in the wavelength range absorbed by this gas decreases, and thus the amount of the received light of the light receiver 2A changes. Whereas, the amount of the received light of the light receiver 2B does not change. Hence, the calculator 40 calculates the difference between the amount of the received light of the light receiver 2A and the amount of the received light of the light receiver 2B, and can obtain, based on the difference, the output corresponding to the concentration of the gas to be detected. Therefore, it is possible to determine that the gas to be detected has flowed into the internal space, and determine the concentration thereof.

When the amount of the light produced by the light emitter 1 is decreased due to a cause (e.g., a variation in a voltage applied to the light emitter 1, a deterioration of the light emitter 1, and pollution of the reflective surface 6) other than the absorption by the gas, the outputs of the light receivers 2A and 2B decrease. Hence, the difference between the amount of the received light of the light receiver 2A and the amount of the received light of the light receiver 2B does not change. Consequently, it is possible to reduce the possibility that the calculator 40 erroneously considers a decrease in the amount of the produced light due to a cause other than the absorption by the gas as the absorption of the light by the gas to be detected.

Alternatively, the optical filters 31 and 32 may be optical bandpass filters for detection, and these bandpass filters transmit light within substantially the same wavelength ranges as the absorption wavelength ranges of different gases to be detected. In this case, the states of the two different gases can be determined.

For example, when a gas (hereinafter referred to as "gas A1") having the absorption wavelength range same as the transmission wavelength range of the optical filter 31 flows into the internal space of the light guiding member 3, the amount of the received light of the light receiver 2A is decreased depending on the concentration of the gas A1. Therefore, the calculator 40 determines the presence of the gas A1 and the concentration thereof based on the output from the light receiver 2A.

In contrast, when a gas (hereinafter referred to as "gas A2") having the absorption wavelength range same as the transmission wavelength range of the optical filter 32 flows into the internal space of the light guiding member 3, the amount of the received light of the light receiver 2B is decreased depending on the concentration of the gas A2. Therefore, the calculator 40 determines the presence of the gas A2 and the concentration thereof based on the output from the light receiver 2B.

As described above, the optical filters 31 and 32 may be optical bandpass filters having wavelength ranges substantially the same as the absorption wavelength ranges of individual gasses. In this case, the calculator 40 can determine the states of various types of gasses.

Note that, in the first modification of the detector A of the present embodiment, the plurality of optical filters 30 (31 and 32) may have the same transmission wavelength range. In this case, the calculator 40 calculates an average of the amount of the received light of the light receiver 2A and the amount of the received light of the light receiver 2B, and can obtain, based on the average, the output corresponding to the concentration of the gas to be detected. Therefore, it is possible to determine that the gas to be detected has flowed into the internal space, and determine the concentration thereof.

Figure 10:
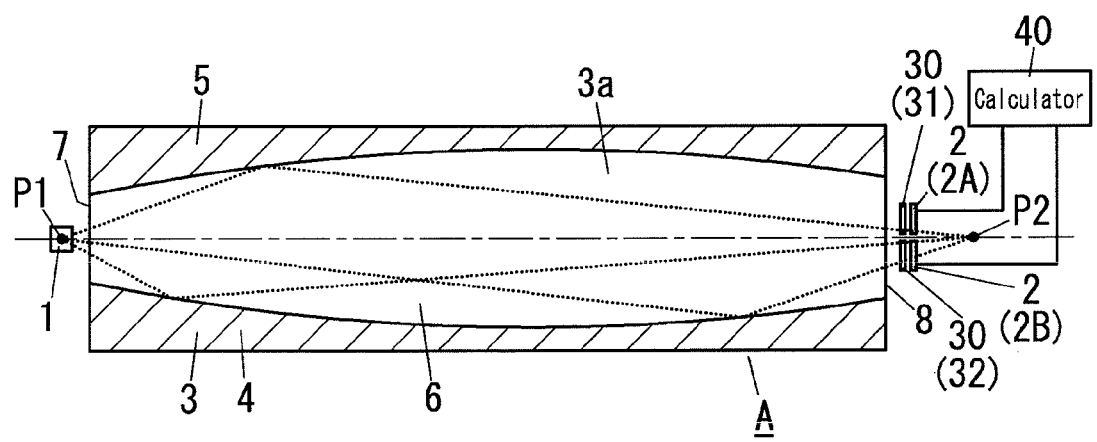
FIG. 10 is a schematic sectional view illustrating the first modification of the detector of the present embodiment.

In FIG. 10, the two sets of the light receiver 2 and the optical filter 30 are situated on the close side of the focal point P2 to the light emitter 1. However, three or more sets of the light receiver 2 and the optical filter 30 may be situated.

In this case, one of the sets may be used as a reference set, and the remaining sets may be used as detection sets. In the reference set, the optical filter 30 may be an optical bandpass filter having the transmission wavelength range different from the absorption wavelength range of the gas to be detected. According to this arrangement, it is possible to determine the states of various types of gasses.

In the detector A illustrated in FIG. 10, the reflective surface 6 is corresponding to a single ellipsoid. However as shown in the second modification of the detector A of the present embodiment illustrated in FIG. 11, the internal surface of the light guiding member 3 (i.e., the internal surface of the detection space 3a) includes reflective surfaces 6A and 6B each having an ellipsoidal shape to share one focal point determined by the point P1 at which the light emitter 1 is situated.

Figure 11:
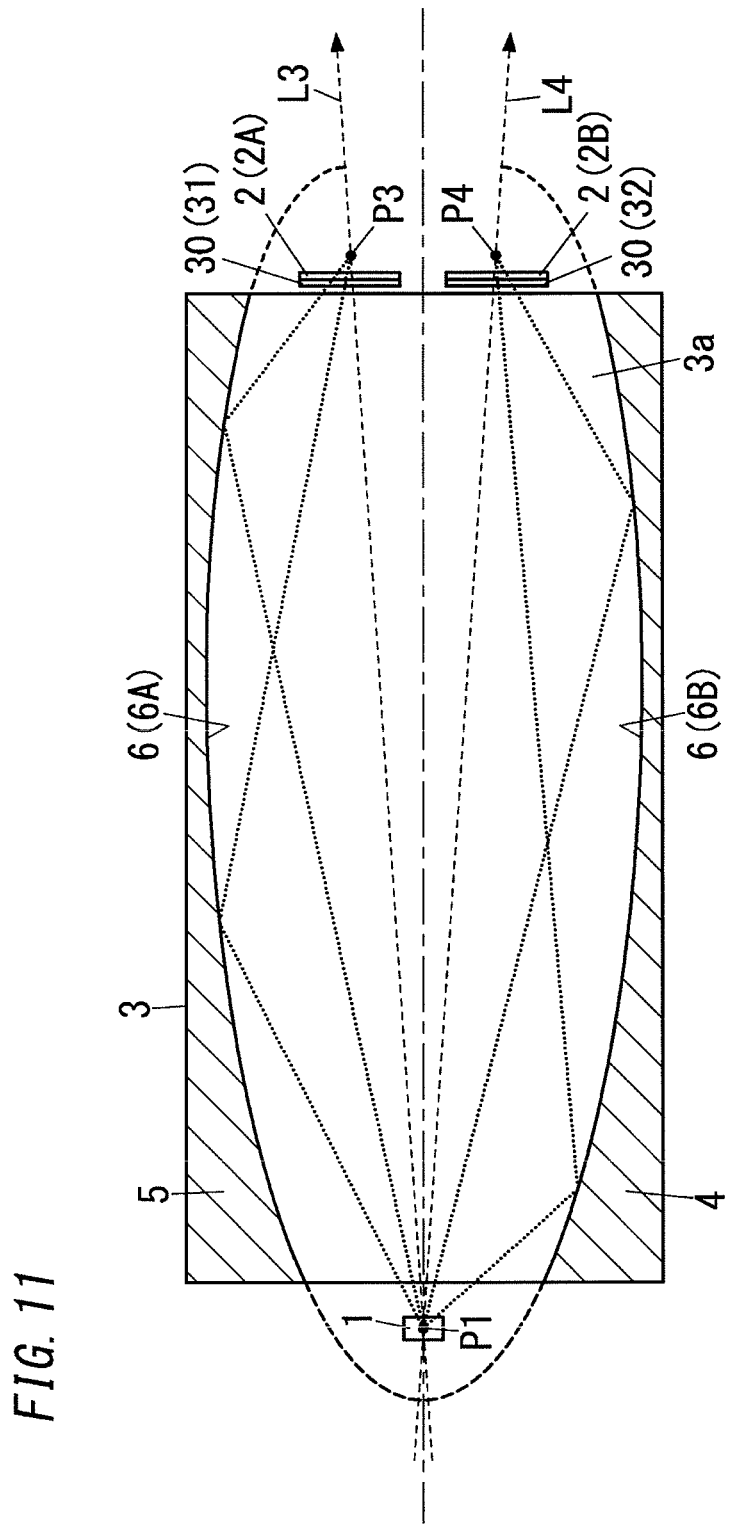
FIG. 11 is a schematic sectional view illustrating the second modification of the detector of the present embodiment.

In the second modification of the detector A of the present embodiment shown in FIG. 11, the light guiding member 3 includes a plurality of reflective surfaces 6. The plurality of reflective surfaces 6 (6A and 6B) are associated with the plurality of light receivers 2 (2A and 2B) individually.

In the second modification, the reflective surface 6A is one (upper surface in FIG. 11) of opposite parts of the internal surface of the detection space 3a in the direction (upward and downward direction in FIG. 11) perpendicular to the axial direction of the light guiding member 3, and the reflective surface 6B is the other (lower surface in FIG. 11) of the opposite parts of the internal surface of the detection space 3a in the direction (upward and downward direction in FIG. 11) perpendicular to the axial direction of the light guiding member 3.

Each of the plurality of reflective surfaces 6 (6A and 6B) is a concave ellipsoidal surface having a long axis defined by a straight line interconnecting an associated one of the plurality of light receivers 2 and the light emitter 1.

In more detail, the reflective surface 6A is the concave ellipsoidal surface having the long axis defined by the straight line L3 interconnecting the associated light receiver 2A and the light emitter 1. The reflective surface 6A has the focal point (first focal point) at the position of the light emitter 1 and the second focal point on the opposite side of the associated light receiver 2A from the first focal point. In FIG. 11, with regard to the reflective surface 6A, the position of the first focal point is represented by the focal position P1, and the position of the second focal point is represented by the position of the focal position P3.

The reflective surface 6B is the concave ellipsoidal surface having the long axis defined by the straight line L4 interconnecting the associated light receiver 2B and the light emitter 1. The reflective surface 6B has the focal point (first focal point) at the position of the light emitter 1 and the second focal point on the opposite side of the associated light receiver 2B from the first focal point. In FIG. 11, with regard to the reflective surface 6B, the position of the first focal point is represented by the focal position P1, and the position of the second focal point is represented by the position of the focal position P4.

As described above, the plurality of reflective surfaces 6 (6A and 6B) have the same first focal point but the different second focal points.

In the second modification described above, the light receiver 2A is on the straight line L3 interconnecting the focal points P1 and P3 of the reflective surface 6A to be on the close side of the focal point P3 to the light emitter 1, and the optical filter 31 is in front of the light receiver 2A. The light receiver 2B is on the straight line L4 interconnecting the focal points P1 and P4 of the reflective surface 6B to be on the close side of the focal point P4 to the light emitter 1, and the optical filter 32 is in front of the light receiver 2B.

In this case, the reflection light caused by reflection of light emitted from the light emitter 1 at the reflective surface 6A is focused into the focal point P3 of the reflective surface 6A. Hence, an amount of the light striking the light receiver 2A in front of the focal point P3 is increased, and thus an incident efficiency of light to the light receiver 2A is improved. Further, the reflection light caused by reflection of light emitted from the light emitter 1 at the reflective surface 6B is focused into the focal point P4 of the reflective surface 6B. Hence, an amount of the light striking the light receiver 2B in front of the focal point P4 is increased, and thus an incident efficiency of light to the light receiver 2B is improved. Note that, in this second modification, the light guiding member 3 may include three or more reflective surfaces 6.

Figure 12:
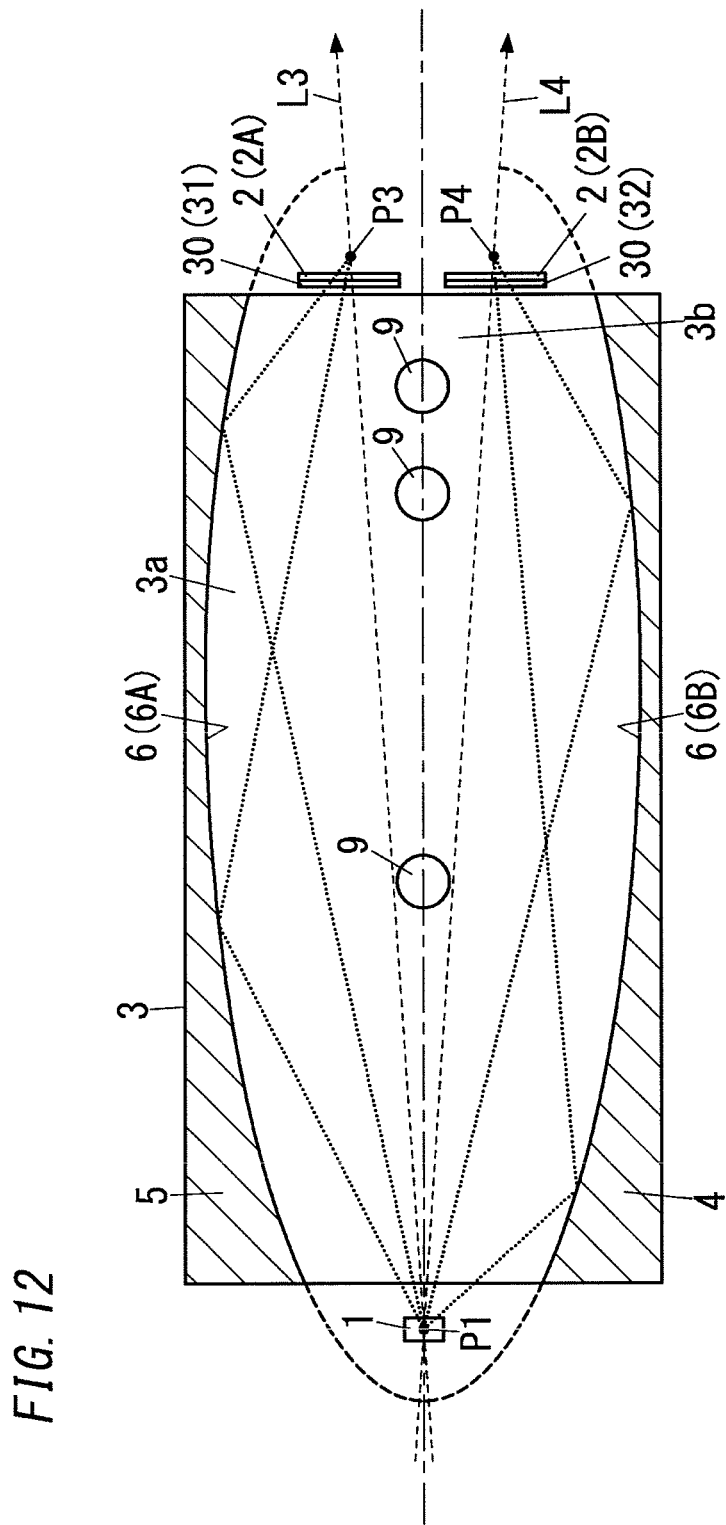
FIG. 12 is a schematic sectional view illustrating the third modification of the detector of the present embodiment.

Further, in the third modification of the detector A of the present embodiment illustrated in FIG. 12, the vents 9 for allowing gas to flow into the internal space are formed in a vicinity (a portion 3b interconnecting the plurality of reflective surfaces 6 (6A and 6B)) of a boundary between the reflective surface 6A provided to a concave internal surface of the upper mirror 5 and the reflective surface 6B provided to a concave internal surface of the lower mirror 4.

In other words, in the third modification of the detector A of the present embodiment shown in FIG. 12, the light guiding member 3 includes the vent 9 allowing the predetermined gas to transfer between the detection space 3a and an external space. The vent 9 is in the portion 3b interconnecting the plurality of reflective surfaces 6 (6A and 6B).

The boundary part between the reflective surfaces 6A and 6B (portion 3b interconnecting the plurality of reflective surfaces 6A and 6B) does not have a perfect ellipsoidal shape. Hence, reflection light caused by reflection of light from the light emitter 1 at a vicinity of the boundary between the reflective surfaces 6A and 6B is unlikely to be focused into the focal points P3 and P4, and thus is not likely to strike the light receivers 2A and 2B.

The vent 9 provided at the vicinity of the boundary between the reflective surfaces 6A and 6B allows gas to flow into the internal space of the light guiding member 3 and to flow outside from the internal space, without causing undesired effects on the amounts of the light striking the light receivers 2A and 2B.

Note that, each of the detectors A shown in FIGS. 11 and 12 includes two sets of the light receiver 2 and the optical filter 30 (the set of the light receiver 2A and the optical filter 31 and the set of the light receiver 2B and the optical filter 32). However, each detector A may include three or more sets of the light receiver 2 and the optical filter 30.

As described above, the detector A of the present embodiment includes the light emitter 1, the light receiver 2, and the light guiding member 3. The light guiding member 3 includes the internal space into which the gas to be detected is to be introduced. The light guiding member 3 reflects light emitted from the light emitter 1 at the reflective surface 6 surrounding the internal space to guide the light to the light receiver 2. The reflective surface 6 is formed into the ellipsoidal shape having the two focal points P1 and P2. The light emitter 1 is disposed at the position of one focal point P1, and the light receiver 2 is disposed on the close side of the position of the other focal point P2 to the light emitter 1.

In other words, the detector A of the present embodiment shown in FIG. 1 includes: the light emitter 1; the at least one light receiver 2; and the light guiding member 3 which includes the detection space 3a for determining the state of the predetermined gas and is configured to guide light emitted from the light emitter 1 to the at least one light receiver 2 through the detection space 3a. The internal surface of the detection space 3a of the light guiding member 3 includes the at least one reflective surface 6 causing reflection of light emitted from the light emitter 1. The at least one reflective surface 6 is the concave ellipsoidal surface having the long axis defined by the straight line determined by the light emitter 1 and the at least one light receiver 2. The at least one reflective surface 6 has the focal point (first focal point) at the position of the light emitter 1 and the second focal point on the opposite side of the at least one light receiver 2 from the first focal point.

As described above, the light emitter 1 is situated at one focal position P1 of the reflective surface 6 and thus light emitted from the light emitter 1 is reflected by the reflective surface 6 and then focused into the other focal position P2.

Additionally, the reflective surface 6 is formed such that the focal position P2 is on the far side of the light receiver 2 from the light emitter 1. Thus, the angle of light incident on the light receiver 2 can be decreased.

In other words, the light receiver 2 is situated on the close side of the further focal position P2 to the light emitter 1 and therefore the incident angle of the light striking the light receiver 2 can be decreased relative to the case where the light receiver 2 is situated at the focal position P2.

Consequently, in contrast to the case where the incident angle is larger, it is possible to reduce a loss caused by reflection of incident light at the surface of the light receiver 2, and therefore the amount of the incident light on the light receiver 2 can be increased. Therefore, it is possible to determine the type and the state (e.g., the concentration) of the gas flowing into the internal space, by use of the output from the light receiver 2.

Moreover, when the optical filter 30 attenuating light of the wavelength that is not in the absorption wavelength range of the gas to be detected is situated in front of the light receiver 2, the incident angle of the light striking the optical filter 30 can be also decreased.

An increase in the incident angle of light on the optical filter 30 causes an increase in the length of the path of this light passing through the filter, and therefore the transmittance of the filter for this light decreases and the transmission wavelength range of the filter for this light changes. Consequently, an amount of undesired light is likely to increase. However, by decreasing the incident angle of the light on the optical filter 30, a mismatch between the transmittance-wavelength characteristics and the absorption wavelength range of the gas to be detected is reduced and therefore the gas to be detected can be successfully detected.

As described above, according to the detector A of the present embodiment, the light emitter 1 is at one focal position P1 and the light receiver 2 is on the close side of the other focal position P2 to the light emitter 1, and therefore it is possible to decrease the incident angle of the light that is reflected by the reflective surface 6 and then strikes the light receiver 2.

Additionally, in a preferred example of the detector A of the present embodiment, the detector A includes the plurality of light receivers 2, the optical filters 30 having the different transmission wavelength ranges are disposed in front of the individual plurality of light receivers 2, and the detector A includes the detection unit 40 configured to determine the state of the gas to be detected, based on the amounts of light received by the plurality of light receivers 2.

For example, the first modification of the detector A of the present embodiment shown in FIG. 10 includes the plurality of light receivers 2. The at least one reflective surface 6 is the concave ellipsoidal surface having the long axis defined by the straight line interconnecting the center of the plurality of light receivers 2 (2A and 2B) and the light emitter 1. Further, the first modification of the detector A of the present embodiment includes: the plurality of optical filters 30 (31 and 32) individually associated with the plurality of light receivers 2 (2A and 2B); and the detection unit 40. Each of the plurality of optical filters 30 is between an associated one of the plurality of light receivers 2 and the light emitter 1. Each of the plurality of light receivers 2 is configured to supply the output corresponding to the amount of the received light to the detection unit 40. The detection unit 40 is configured to determine the state of the predetermined gas based on the outputs received from the plurality of light receivers 2.

According to this configuration, it is possible to determine the presence or absence of each of various types of gas and the concentration thereof, by use of the amounts of light received by the individual light receivers 2.

When the amounts of the light received by the light receivers 2 are changed due to a cause (e.g., a variation in a voltage applied to the light emitter 1, a deterioration of the light emitter 1, and pollution of the reflective surface 6) other than the absorption by the gas, changes in the amounts of the light received by the plurality of light receivers 2 are substantially the same level. Hence, by using the outputs from the plurality of light receivers 2, it is possible to reduce the possibility that the detector erroneously determines that the gas has flowed into the internal space, based on decreases in the amounts of the received light due to a cause other than the absorption by the gas.

The optical bandpass filter shows the different transmission wavelength range with regard to the light striking the optical filter 30 at the larger incident angle, and therefore the amount of the undesired light increases. However, by decreasing the incident angle of the light on the optical filter 30, a difference in the transmittance-wavelength characteristics is reduced and therefore the gas to be detected can be successfully detected.

Accordingly the detector of the present embodiment can reduce the incident angle of the light striking the optical filter 30 (i.e., the angle between the incident direction of the light on the optical filter 30 and the optical axis of the optical filter). Hence, the optical filter 30 can show the desired transmittance-wavelength characteristics, and therefore the S/N ratio can be improved. Additionally, it is possible to decrease an amount of light (infrared light) reflected by a surface of the optical filter.

Moreover, in the first modification of the detector A of the present embodiment, the plurality of optical filters 30 (31 and 32) have the different transmission wavelength ranges. Alternatively, the plurality of optical filters 30 (31 and 32) may have the same transmission wavelength range.

Additionally, with regard to the detector A including a plurality of sets of the light receiver 2 (2A, 2B) and the optical filter 30 (31, 32), it is preferable that the reflective surfaces 6 include the plurality of reflective surfaces 6 (6A and 6B) having the ellipsoidal shapes having the central axes defined ty the straight lines (L3 and L4) interconnecting the light receivers 2 (2A and 2B) and the light emitter 1.

For example, the second modification of the detector A of the present embodiment shown in FIG. 11 has substantially the same structure as the structure of the detector A of the present embodiment shown in FIG. 1, but includes the plurality of light receivers 2. The light guiding member 3 includes the plurality of reflective surfaces 6. The plurality of reflective surfaces 6 (6A and 6B) are associated with the plurality of light receivers 2 (2A and 2B) individually. Each of the plurality of reflective surfaces 6 is the concave ellipsoidal surface having the long axis defined by the straight line interconnecting the associated one of the plurality of light receivers 2 and the light emitter 1. Each of the plurality of reflective surfaces 6 has the focal point (first focal point) at the position of the light emitter 1 and the second focal point on the opposite side of the associated one of the plurality of light receivers 2 from the first focal point.

In other words, the second modification of the detector A of the present embodiment shown in FIG. 11 includes: the light emitter 1; the plurality of light receivers 2 (2A and 2B); and the light guiding member 3 which includes the detection space 3a for determining the state of the predetermined gas and is configured to guide light emitted from the light emitter 1 to the plurality of light receivers 2 (2A and 2B) through the detection space 3a. The internal surface of the detection space 3a of the light guiding member 3 includes the plurality of reflective surfaces 6 (6A and 6B) each causing reflection of light emitted from the light emitter 1. The plurality of reflective surfaces 6 (6A and 6B) are associated with the plurality of light receivers 2 (2A and 2B) individually. Each of the plurality of reflective surfaces 6 is the concave ellipsoidal surface having the long axis defined by the straight line interconnecting the associated one of the plurality of light receivers 2 and the light emitter 1. Each of the plurality of reflective surfaces 6 has the focal point (first focal point) at the position of the light emitter 1, and the second focal point on the opposite side of the associated one of the plurality of light receivers 2 from the first focal point.

Accordingly, in the second modification of the detector A of the present embodiment, each of the plurality of reflective surfaces 6 has the second focal point on the opposite side of the associated one of the plurality of light receivers 2 from the first focal point. Alternatively, each of the plurality of reflective surfaces 6 has the second focal point at the position of the associated one of the plurality of light receivers 2.

Further, the second modification of the detector A of the present embodiment includes: the plurality of optical filters 30 (31 and 32) individually associated with the plurality of light receivers 2 (2A and 2B); and the detection unit 40. Each of the plurality of optical filters 30 is between the associated one of the plurality of light receivers 2 and the light emitter 1. Each of the plurality of light receivers 2 is configured to supply the output corresponding to the amount of the received light to the detection unit 40. The detection unit 40 is configured to determine the state of the predetermined gas based on the outputs received from the plurality of light receivers 2.

Moreover, in the second modification of the detector A of the present embodiment, the plurality of optical filters 30 (31 and 32) have the different transmission wavelength ranges. Alternatively, the plurality of optical filters 30 (31 and 32) may have the same transmission wavelength range.

Hence, the amounts of the light incident on the individual light receivers 2A can be increased, and thus the incident efficiencies of light to the individual light receivers 2 are improved.

Additionally, with regard to the detector A, it is preferable that the vent 9 allowing passage of gas be in the vicinity of the boundary between the plurality of reflective surfaces 6.

For example, according to the third modification of the detector A of the present embodiment shown in FIG. 12 includes, in addition to the second modification, the light guiding member 3 includes the vent 9 allowing the predetermined gas to move between the detection space 3a and the external space. The vent 9 is in the portion 3b interconnecting the plurality of reflective surfaces 6.

The vicinity of the boundary part between the reflective surfaces 6A and 6B (i.e., a part near the portion 3b interconnecting the plurality of reflective surfaces 6A and 6B) does not have a perfect ellipsoidal shape. Hence, light reflected by a vicinity of the boundary between the reflective surfaces 6 is unlikely to be incident on the light receivers 2.

The vent 9 provided at the vicinity of the boundary between the reflective surfaces 6 allows gas to flow into the internal space 3a of the light guiding member 3 and to flow outside from the internal space 3a, without causing undesired effects on the amounts of the light incident on the light receivers 2.

The invention claimed is:
1. A detector, comprising:
a light emitter;
a plurality of light receivers; and
a light guiding member which includes a detection space for determining a state of a predetermined gas and is configured to guide light emitted from the light emitter to the plurality of light receivers through the detection space,
an internal surface of the detection space of the light guiding member including a plurality of reflective surfaces associated with the plurality of light receivers individually and causing reflection of light emitted from the light emitter,
each of the plurality of reflective surfaces being a concave ellipsoidal surface having a long axis defined by a straight line interconnecting an associated one of the plurality of light receivers and the light emitter, and
each of the plurality of reflective surfaces having a first focal point at a position of the light emitter and a second focal point on an opposite side of an associated one of the plurality of light receivers from the first focal point,
the light guiding member including a vent allowing the predetermined gas to transfer between the detection space and an external space, and
the vent being in a portion interconnecting the plurality of reflective surfaces.
2. The detector according to claim 1, wherein:
each of the plurality of reflective surfaces being a concave ellipsoidal surface having a long axis defined by a straight line interconnecting a center of an associated one of the plurality of light receivers and the light emitter.

3. The detector according to claim 2, wherein:
the detector comprises
    a plurality of optical filters individually associated with the plurality of light receivers, and
    a detection unit;
each of the plurality of optical filters is between an associated one of the plurality of light receivers and the light emitter;
each of the plurality of light receivers is configured to supply an output corresponding to an amount of received light to the detection unit; and
the detection unit is configured to determine a state of the predetermined gas based on the outputs received from the plurality of light receivers.

4. The detector according to claim 3, wherein
the plurality of optical filters have different transmission wavelength ranges.

5. The detector according to claim 3, wherein
the plurality of optical filters have the same transmission wavelength range.

6. A detector, comprising:
a light emitter;
a plurality of light receivers;
a light guiding member which includes a detection space for determining a state of a predetermined gas and is configured to guide light emitted from the light emitter to the at least one light receiver through the detection space;
a plurality of optical filters individually associated with the plurality of light receivers; and
a detection unit,
an internal surface of the detection space of the light guiding member including at least one reflective surface causing reflection of light emitted from the light emitter,
the at least one reflective surface being a concave ellipsoidal surface having a long axis defined by a straight line interconnecting a center of the plurality of light receivers and the light emitter,
the at least one reflective surface having a first focal point at a position of the light emitter and a second focal point on an opposite side of the at least one light receiver from the first focal point,
each of the plurality of optical filters being between an associated one of the plurality of light receivers and the light emitter,
each of the plurality of light receivers being configured to supply an output corresponding to an amount of received light to the detection unit, and
the detection unit being configured to determine a state of the predetermined gas based on the outputs received from the plurality of light receivers.

7. The detector according to claim 6, wherein:
the detector comprises a plurality of light receivers;
the light guiding member including a plurality of reflective surfaces;
the plurality of reflective surfaces are associated with the plurality of light receivers individually;
each of the plurality of reflective surfaces is a concave ellipsoidal surface having a long axis defined by a straight line interconnecting an associated one of the plurality of light receivers and the light emitter; and
each of the plurality of reflective surfaces has the first focal point at the position of the light emitter and the second focal point on an opposite side of an associated one of the plurality of light receivers from the first focal point.

8. The detector according to claim 6, wherein
the plurality of optical filters have different transmission wavelength ranges.

9. The detector according to claim 6, wherein
the plurality of optical filters have the same transmission wavelength range.

* * * * *